United States Patent [19]

Sliski

[11] Patent Number: 5,623,139

[45] Date of Patent: Apr. 22, 1997

[54] CCD X-RAY MICRODENSITOMETER SYSTEM

[75] Inventor: Alan P. Sliski, Lincoln, Mass.

[73] Assignee: Photoelectron Corporation, Lexington, Mass.

[21] Appl. No.: 286,285

[22] Filed: Aug. 5, 1994

[51] Int. Cl.$^6$ ..................................................... G01J 1/32
[52] U.S. Cl. .................. 250/205; 250/208.1; 250/578.1; 250/341.7; 250/553
[58] Field of Search ..................................... 250/552, 553, 250/555, 556, 559, 566, 571, 370.07, 341.7, 208.1, 205, 578.1

[56] References Cited

U.S. PATENT DOCUMENTS

| | | |
|---|---|---|
| Re. 31,847 | 3/1985 | Luckey . |
| 3,031,575 | 4/1962 | Gevantman et al. . |
| 3,582,219 | 6/1971 | Pfeifer . |
| 3,652,850 | 3/1972 | Briggs .................................. 250/341.7 |
| 3,802,784 | 4/1974 | Reynolds et al. ..................... 356/432 |
| 3,856,398 | 12/1974 | Taylor . |
| 4,717,258 | 1/1988 | Sutton . |
| 4,900,930 | 2/1990 | Takiguchi et al. . |
| 4,939,709 | 7/1990 | Doyle . |
| 5,005,592 | 4/1991 | Cartmell . |
| 5,021,978 | 6/1991 | Stone et al. . |
| 5,119,132 | 6/1992 | Butler ..................................... 250/205 |
| 5,255,069 | 10/1993 | Duarte . |
| 5,296,701 | 3/1994 | Kirkman et al. ..................... 250/223 B |
| 5,365,066 | 11/1994 | Krueger, Jr. et al. ................. 250/341.7 |
| 5,447,811 | 9/1995 | Buhr et al. ................................ 430/20 |

OTHER PUBLICATIONS

Medical Physics, vol. 20, No. 3, May/Jun. 1993, pp. 925–926.

*Primary Examiner*—Stephone Allen
*Attorney, Agent, or Firm*—Lappin & Kusmer LLP

[57] ABSTRACT

A system is disclosed for producing images representing radiation dose distributions in order to verify the radiation dose applied to a target area. The system uses a phantom assembly constructed of material that is the radiological equivalent of live tissue. The phantom assembly has slits where radiation sensitive film can be inserted and can include a channel for an insertable radiation generating device. The treatment dose is then applied to the phantom and the radiation sensitive film records the dose. A CCD camera microdensitometer is then used to read the exposed radiation sensitive film. The CCD camera microdensitometer includes a computer system which processes the image to remove artifacts and generates isodose contours for the radiation treatment applied. In addition, several pieces of radiation sensitive film in different planes can be exposed and processed in order to produce images representing the radiation dose distribution in three dimensions.

13 Claims, 6 Drawing Sheets

CCD X-RAY MICRODENSITOMETER SYSTEM

BACKGROUND OF THE INVENTION

This invention relates to a device for measuring two and three dimensional radiation dose distributions for radiation generating devices. Specifically, the invention relates to a system for recording the dose of radiation delivered to a target area and utilizing one or more recordings to measure radiation dose distributions for the tissue in and adjacent to the target area.

In the field of medicine, radiation is used for diagnostic, therapeutic and palliative treatment of patients. The conventional medical radiation sources used for these treatments include large fixed position machines as well as small, transportable radiation generating probes. The current state of the art treatment systems utilize computers to generate complex treatment plans that are difficult and sometimes impossible to verify using conventional measurement techniques such as ionization chambers which only record the dose at one point in space.

In order to be able to more precisely control the dosage and area of treatment, it is necessary to accurately measure and verify the dose distribution and precisely calibrate the device. This procedure is further complicated by fact that the radiation dosage is affected by the density of the material, the more dense the material the more radiation it will absorb. Therefore it is desirable to model the area to be irradiated in order to verify the proper radiation dose is being applied.

Accordingly, it is an object of this invention to provide an apparatus for measuring the dose distribution for radiation applied to a target area.

It is another object of the invention to provide an apparatus for measuring and recording the dose distribution and generating an image representing the dose distribution of radiation applied to a localized area.

It is another object of the invention to provide an apparatus for measuring and recording the dose distribution and generating an image representing the dose distribution of a miniaturized radiation source in a target area.

It is another object of the invention to provide an apparatus which is capable of measuring and recording the dose distribution and generating an image representing the dose distribution of a predefined radiation treatment plan applied to a medium having known density and radiation absorption characteristics.

It is yet another object of the invention to provide an apparatus which is capable of measuring and recording and generating a three dimensional image representing the dose distribution of radiation applied to a target area.

SUMMARY OF THE INVENTION

The invention relates to a phantom assembly and a microdensitometer. The phantom assembly supports radiation sensitive film in one or more predefined planes and optionally includes a channel for the insertion of a miniaturized radiation source. One preferred radiation sensitive film is radiochromic film. Radiochromic film is a special film used to measure the dose of ionizing radiation delivered to an area and does not require subsequent processing to develop the image. The optical density of the exposed film is proportional to the dose of ionizing radiation received. The radiochromic film is exposed by the radiation source. The radiochromic film is read by the microdensitometer and used to produce isodose contours and a three dimensional representation of the dose distribution.

The phantom assembly is preferably constructed of a tissue equivalent material and formed in substantially the same physical dimensions as the tissue being treated. The phantom assembly includes one or more locations where radiochromic film can be inserted for exposure. Preferably, several pieces of film, each parallel to a common plane but spaced apart at predetermined distances from the target area can be provided. Alternatively, the film can be oriented in three orthogonal planes for measuring the radiation dose applied to the target area in three dimensions.

The microdensitometer consists of a CCD Camera and a uniform light source connected by an optical rail. The CCD Camera is connected to a computer system which processes the image. The optical rail allows the camera to be moved with respect to the light source to change the magnification of the image while maintaining the camera in fixed alignment. The uniform light source includes a light box enclosing multiple light generating elements and a light diffusing element. The wavelength of the light generating elements is matched to the peak absorption wavelength of the exposed radiochromic film. The light generating elements and the diffusing element are designed to provide uniformity of better than 10% in the central area of the light box. The light generating elements are arranged in substantially annular arrays varying with intensity. The annular array with the highest intensity being adjacent the outer edges of the uniform light source. A current control circuit can be provided to adjust the light intensity and optimize the image for the dynamic range of the CCD camera. A photo-sensing element can also be provided to regulate the light intensity. The computer system acquires images from the camera and processes the images to produce isodose contours.

In order to obtain accurate profiles, the image is processed to compensate for various sources of error and noise. Dark image acquisition errors appear as differences in pixel values for the same level dark image. The system reads a pure black image and stores the dark value for each pixel and uses these dark values to compensate the image. The light image acquisition errors appear as differences in pixel values for the same level light image. They can also be caused by imperfections in the camera lens and non-uniformity of the light source. The system reads a light image and stores the individual light values for each pixel and uses these light values to compensate the image. Frame transfer errors occur when the CCD Camera takes a new image, the camera clocks in a blank image causing some image smearing. The system compensates for this error by first taking a short exposure and subtracting it from the second longer exposure. Scatter compensation error is caused by reflections from the surface of the camera lens, dust on the lens and the surface finish of the lens surfaces. To compensate for scatter error, an opaque object is imaged and a scatter compensation factor is generated as the average pixel value for the area of the opaque object divide by the average pixel value for the entire image. In addition, the system can scan same image of the film several times and take an average of the several scans.

BRIEF DESCRIPTION OF THE DRAWINGS

The foregoing and other objects of this invention, the various features thereof, as well as the invention itself, may be more fully understood from the following description, when read together with the accompanying drawings in which.

DETAILED DESCRIPTION OF THE PREFERRED EMBODIMENTS

The microdensitometer system provides a means for acquiring the images recorded on radiation sensitive film by reading them into a computer. The computer can then use conventional image processing techniques to produce iso-dose contours or images representing dose distribution in three dimensions.

Figure 1:
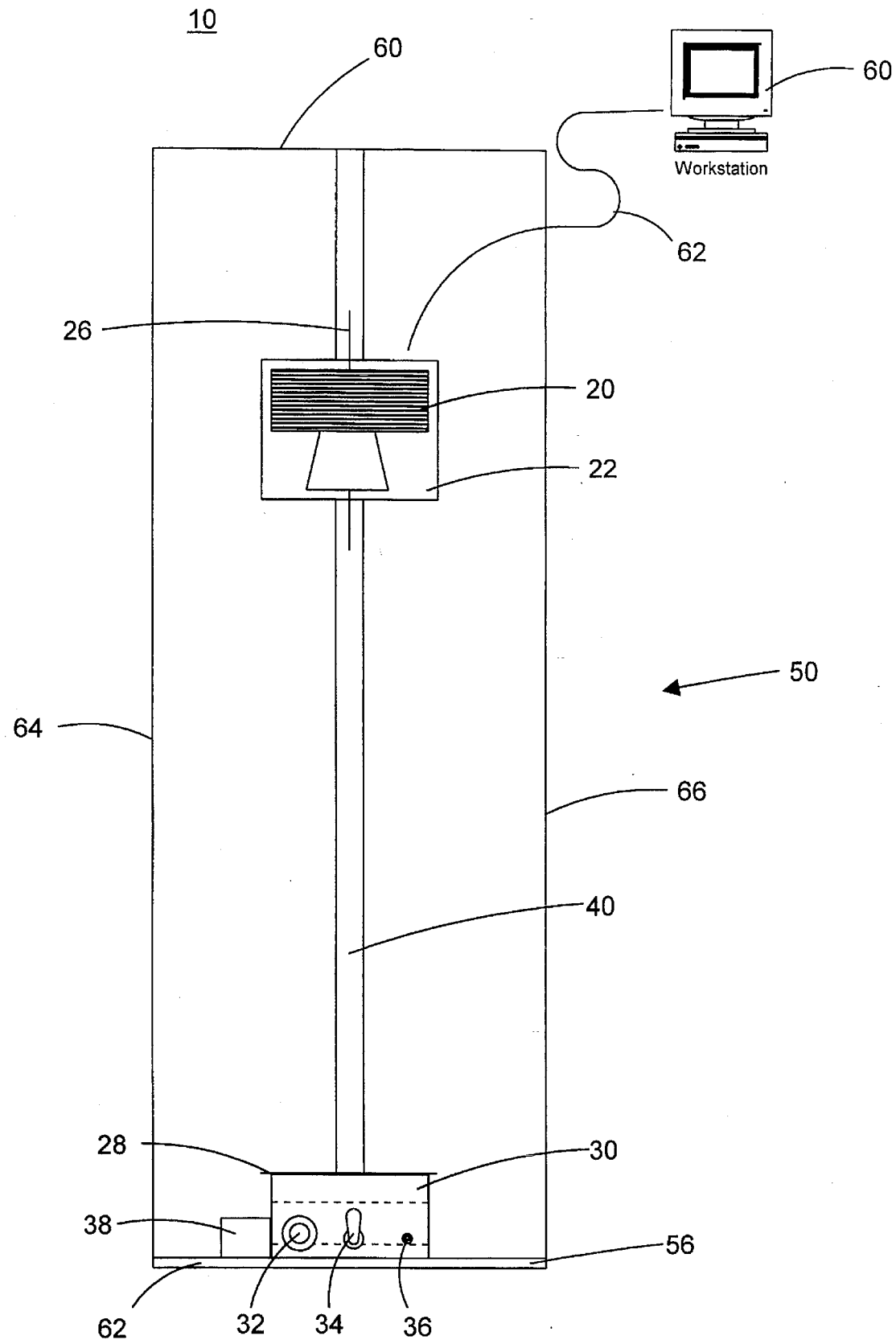
FIG. 1 is a diagrammatic front view of a CCD Camera Microdensitometer in accordance with invention, the front door had been removed to facilitate comprehension.
Figure 2:
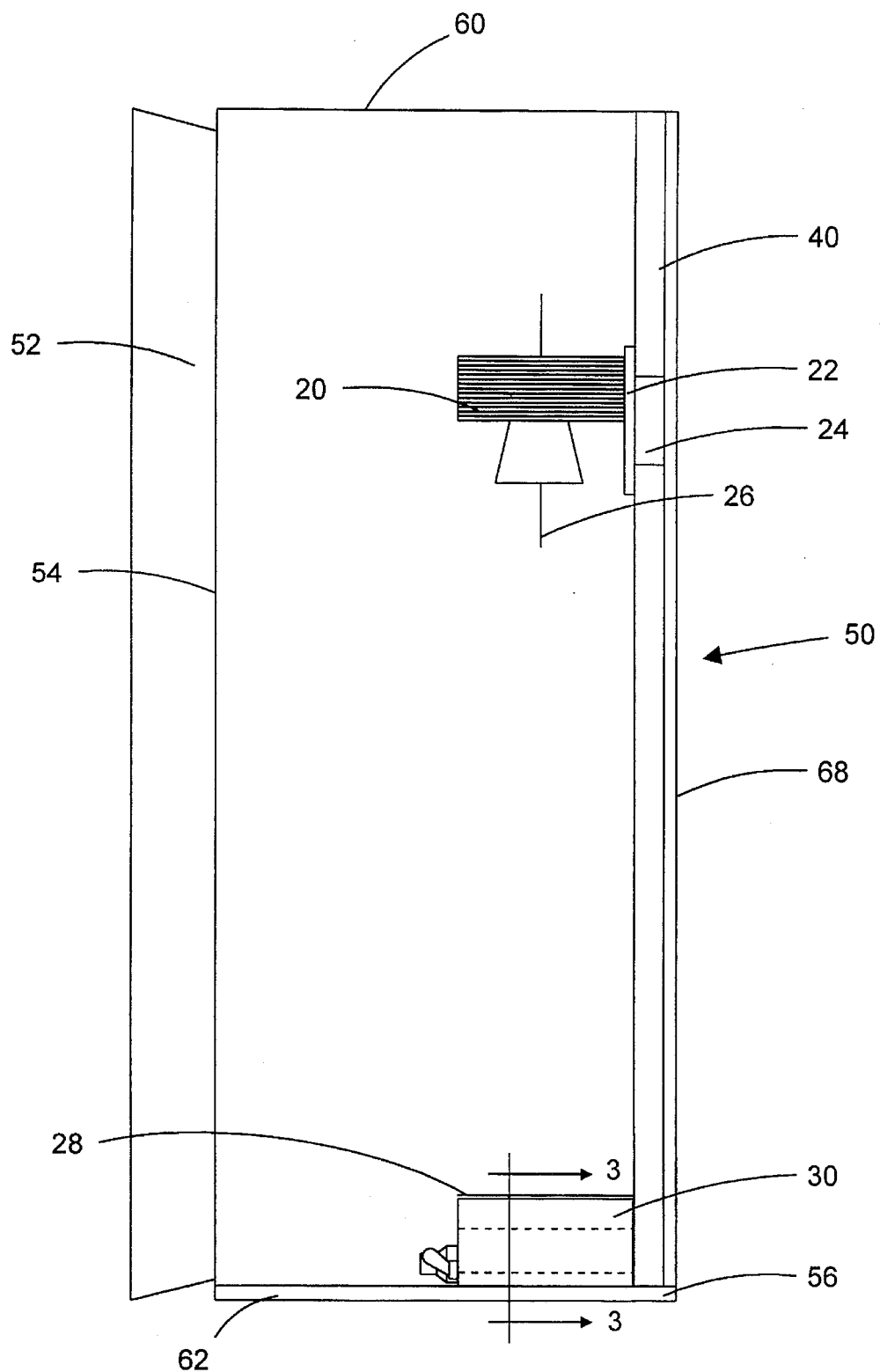
FIG. 2 is a diagrammatic side view of the CCD Camera Microdensitometer of FIG. 1 in accordance with invention, the right side panel has been removed to facilitate comprehension.

As shown in FIGS. 1 and 2, the microdensitometer system includes a highly uniform light source 30 and a charge coupled device (CCD) camera 20 both coupled to an optical rail 40. The CCD camera 20 is directed along a principal axis 26 to the uniform light source 30. An imaging plane 28 is located between the CCD camera 20 and the uniform light source 30. Preferably, the imaging plane 28 coincides with the top surface of the uniform light source 30. A light tight enclosure 50 is also provided to block out ambient light that could affect the camera 20 readings. The CCD camera 20 is interconnected via a cable 62 to a computer system 60.

The light tight enclosure 50 includes a top wall 60, a bottom wall 62 and four lateral side walls, front 52, left 64, right 66, and rear 68. The front wall 52 is attached to the right side wall 66 by a hinge 54 and serves as a door. Adjacent the rear wall 68 is a rail 40 and a camera mounting element 22 that can be adjustably positioned along the rail 40. In one embodiment, the rail 40 is a cylindrical tube and the camera mounting element 22 includes a locking collar 24 that can be tightened around the tube 40. Either the rail 40 or the rear wall 68 adjacent the rail 40 can be provided with indicia 42 for indicating the distance from the camera 20 focal plane to the imaging plane 28 on the light source or indicating the relative magnification of the camera lens.

Preferably, the uniform light source 30 includes a locking element 38 for locking it in position in the light tight enclosure 50. This prevents any slight movement of the light source which would require recalibration of the system. In the preferred embodiment, the light tight enclosure 50 includes a steel baseplate 56 and the light source 30 includes a releasable magnetic clamp 38 which can engage the baseplate 56 and lock the light source 30 in place.

The radiation sensitive film can be either silver halide based films or radiochromic films. Radiochromic films are preferred because they provide several advantages over silver halide based films. Radiochromic films do not require subsequent processing to develop the image and they are not substantially affected by ambient light. In addition, the peak absorption wavelength of the radiochromic film can be selected based on the radiochromic dye used.

The light source 30 produces a specific wavelength of light that is highly uniform over a predefined area. Preferably, the wavelength is carefully chosen to match the peak absorption wavelength of the radiochromic film. In the preferred embodiment, the light source 30 uses GaAlAs LEDs to produce red light at a wavelength of 660 nanometers which is optimally matched to the radiochromic film selected. The preferred radiochromic film is GAFchromic film available from ISP Corporation of Wayne, N.J. The GaAlAs LEDs are type LN28WAL available from Panasonic Corporation of Japan.

Alternatively, the light source 30 can use Silicon Carbide LEDs to produce blue light at a wavelength of 470 nanometers which is optimally matched to a film having a peak absorption wavelength of 470 nanometers. In an alternative embodiment, blue light, such as that produced by the silicon carbide LEDs, can be used with film having a red peak absorption wavelength in order to extend the dynamic range of the measurement system.

Figure 3:
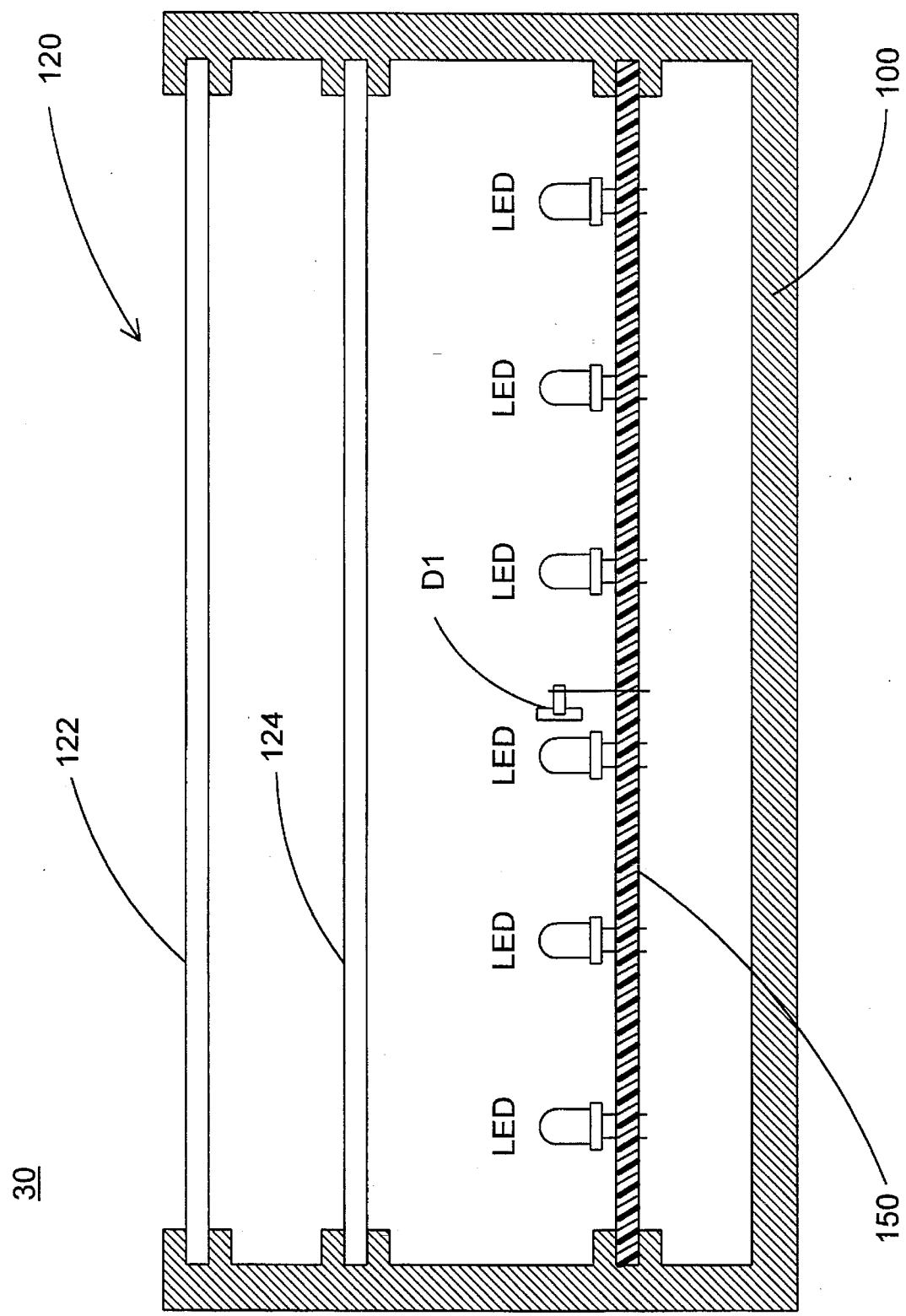
FIG. 3 is section view of the light box along line 3—3 of FIG. 2.

FIG. 3 shows the highly uniform light source 30 which includes a light box 100 housing a plurality of light generating elements LED and a diffuser 120 arranged and configured to produce light uniformly over the top surface. The light box 100 includes a bottom wall, and four side walls. A circuit board 150 carrying an array of light emitting diodes (LEDs) LED is supported by channels in the side walls near the bottom of the light box. Preferably, the inside surfaces of the light box are made as shiny as possible to facilitate producing light uniformly. The light box also holds a diffuser 120 which further aids in providing light uniformly. In the preferred embodiment, the diffuser 120 includes one piece of frosted glass 122 and one piece of opal glass 124. The upper diffuser 122 is positioned as the top of the light box and the lower diffuser 124 is placed approximately half way between the upper diffuser 122 and the circuit board 150. The upper diffuser 122 also serves to support the radiochromic film for imaging.

Figure 4:
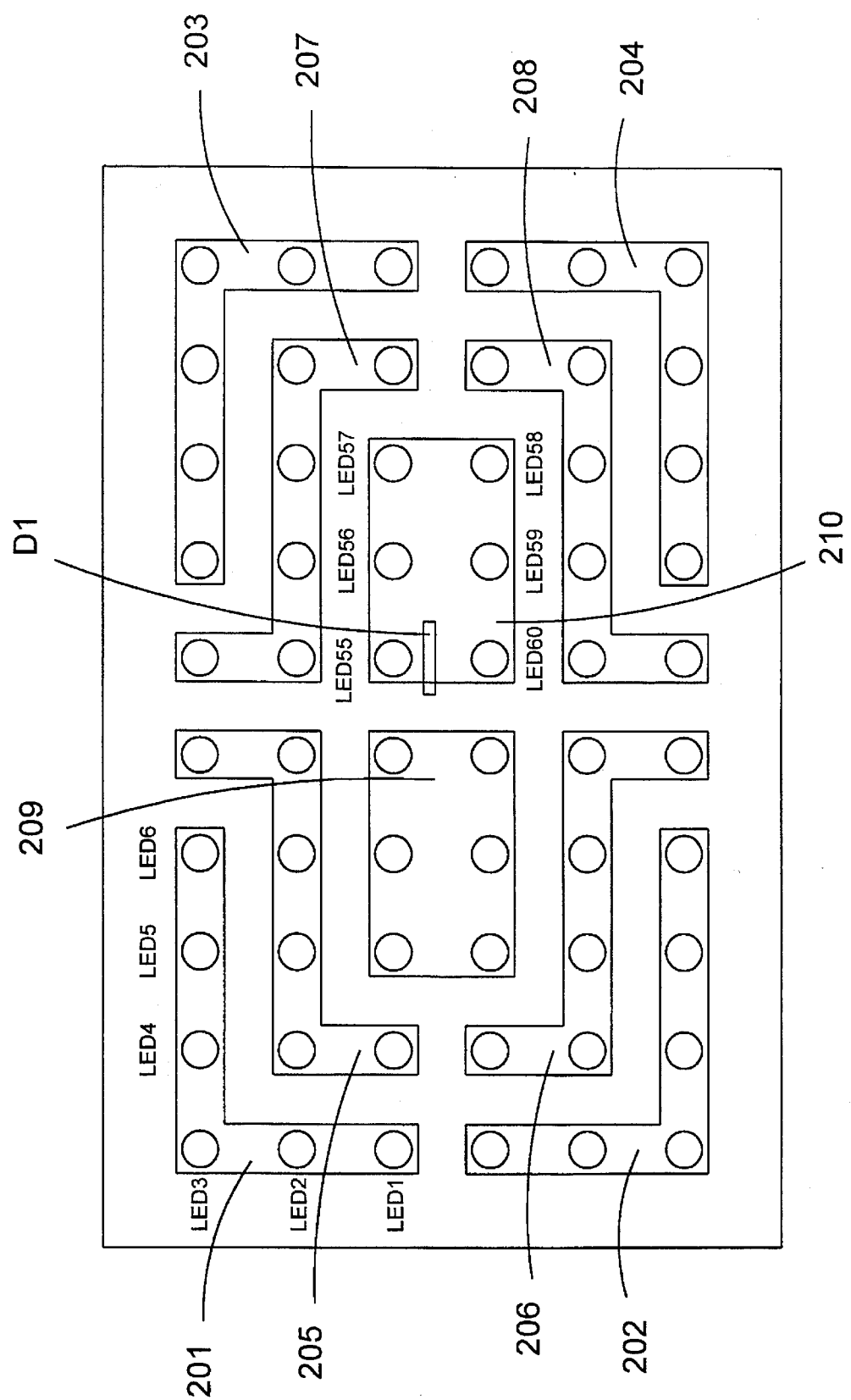
FIG. 4 is a diagrammatic view of the circuit board showing the groupings of LEDS in accordance with the invention.
Figure 5:
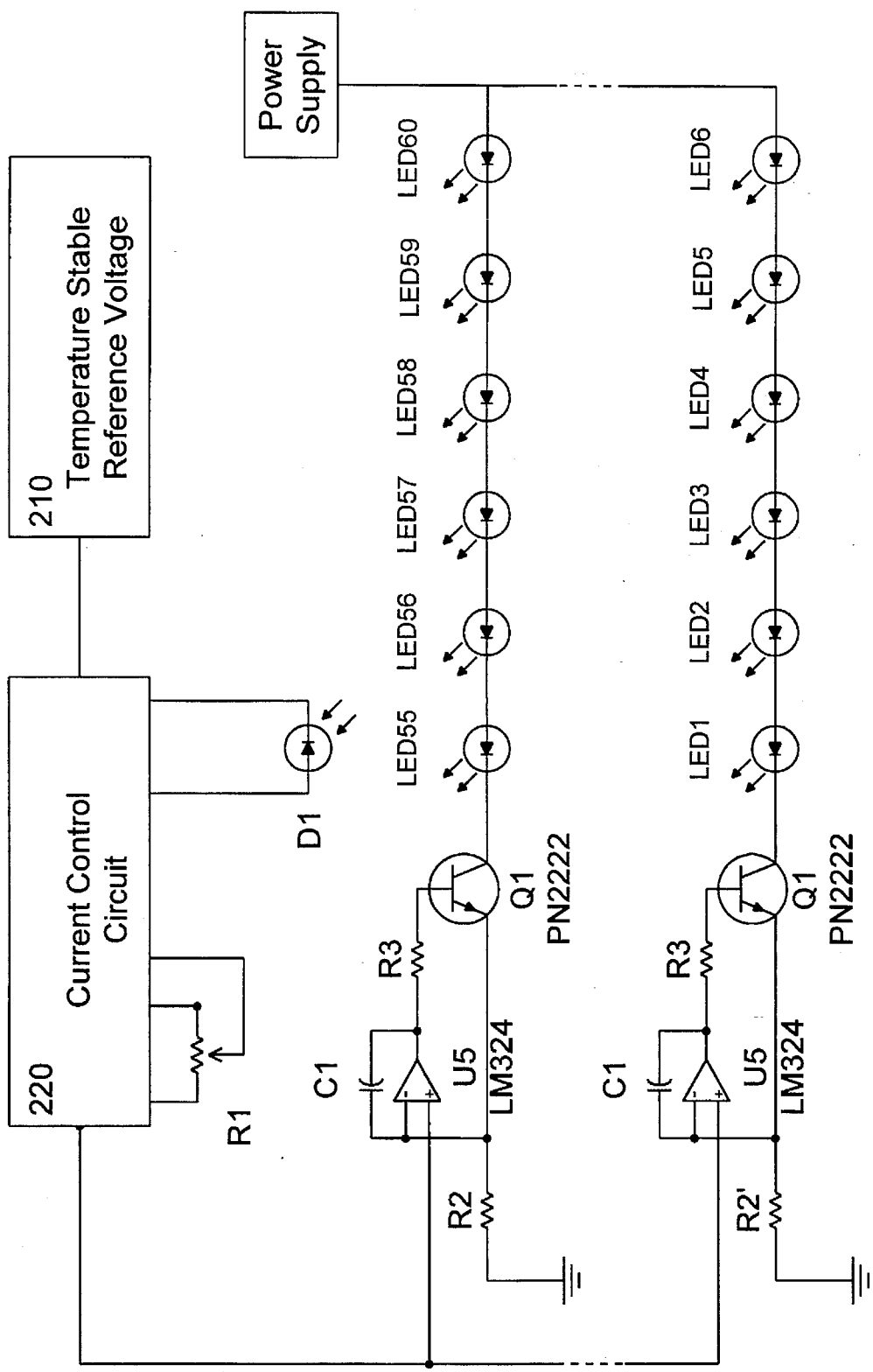
FIG. 5 is diagram showing the LED current control circuit.

As shown in FIG. 4, one preferred embodiment of the circuit board includes a rectangular matrix of sixty LEDs arranged in a planar, substantially annular array of ten groups of six LEDs 210—210. The current to each group of LEDs is chosen to precisely control the amount of light produced by each group. In this embodiment, three different levels of current are applied to three annular areas in order to produce a substantially uniform source of light. As shown in FIG. 5, this is accomplished by using three different current sensing resistors R2, R2' values in the circuits in each of the different annular areas. In the preferred embodiment, the current limiting resistor values are: 20 ohms for the outer most groups 201, 202, 203, and 204; 42.2 ohms for the middle groups 205, 206, 207, and 208 and 75.8 ohms for the inner most groups 209 and 210. Alternatively, the uniformity of the matrix of LEDs can be controlled by driving all the LEDs at the same current and properly selecting the spaces between adjacent LEDs to produce uniform intensity. In addition, the LEDs can be arranged in a substantially circular array and/or mounted in a cylindrical housing.

FIG. 4 also shows a photodiode D1 mounted on the circuit board 150 adjacent one of the LEDs LED55. The photodiode D1 is used in conjunction with a current control circuit to regulate the level of intensity of the LEDs. A potentiometer R1 can also be provide to permit manual adjustment of the relative intensity of the light source. By adjusting the potentiometer R1, the intensity can be adjusted to optimize the light source and resulting image for the dynamic range of the camera.

FIG. 5 shows a diagram of the circuit 200 for driving the LEDs. In order to produce a highly stable light source, the circuit includes a highly stable temperature compensated voltage reference 210. The circuit 200 also includes a current controlling circuit 220 which uses the photodiode D1 and the potentiometer R1. The photodiode D1 monitors the LED output and produces a signal representative of the LED intensity. The current control circuit detects any change in intensity and controls the current ensure that the light output is stable. The potentiometer R1 allows the LED output to be manually adjusted in order to optimize the light source 30 for the maximum dynamic range of the CCD camera 20.

Figure 6:
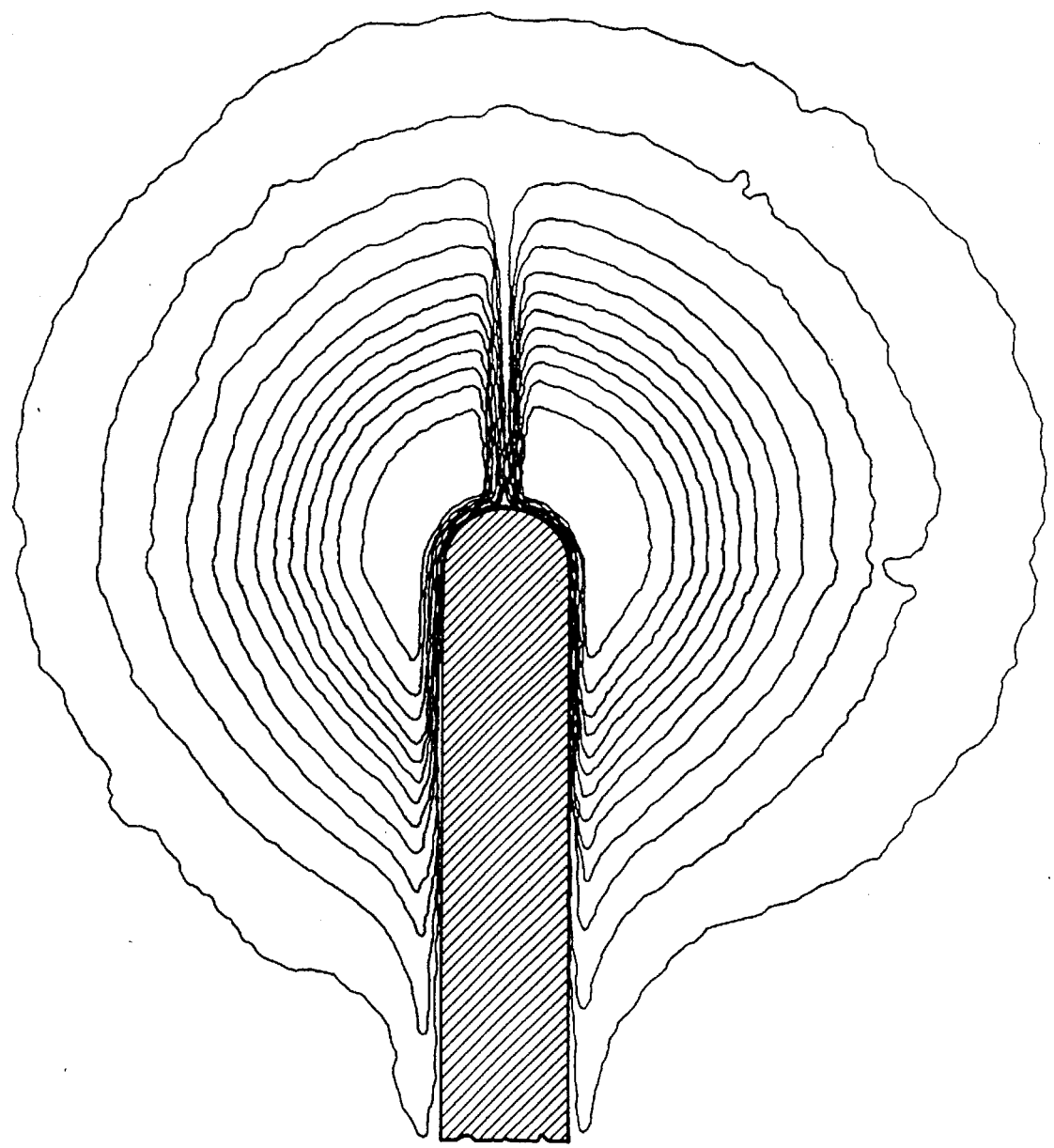
FIG. 6 is a representation of an image produced with the CCD Microdensitometer System in accordance with the invention.

FIG. 6 shows the resulting image produced by processing a single piece of radiochromic film. The dark lines are isodose contours. The image can also be rendered in color whereby the different colors represent predefined levels of absorbed radiation. Several such images from different planes can be combined using conventional computed image rendering techniques to produce a three dimensional representation of the radiation dose distribution.

In the preferred embodiment, the camera 20 is 242 by 375 pixel CCD camera capable of 16 bit resolution. The preferred camera is ST-6 available from the Santa Barbara Instrument Group of Santa Barbara, Calif. The computer is a desktop personal computer such as an IBM compatible personal computer or an APPLE Macintosh personal computer. Preferably, the computer is an Intel i486 based IBM compatible personal computer. The image processing software is MIRA available from Axiom Research, Inc. of Phoenix, Ariz.

In operation, the system is used to read an image recorded on a piece of radiochromic film. First the light source 30 is positioned under the camera 20 and locked in place. Next the camera 20 is adjusted to a position along the optical rail 40 for proper magnification and the camera lens is focused on the image plane 28. The system is then calibrated for dark imaging acquisition, light image acquisition, frame transfer compensation and scatter compensation. The film is placed on the upper surface of the light source 30. The camera reads the image and the computer processes the image to compensate for imaging errors determined during calibration.

Dark image acquisition error is compensated for by reading a dark image and recording dark level for each pixel. The computer system stores this compensation factor for each pixel and applies it by subtracting the corresponding compensation factor from each pixel value for the image being processed. This dark image error compensation factor will need to be recalibrated if either the CCD camera temperature or shutter speed changes. In the preferred embodiment, several dark images are read and the average over the several images is used to generate the dark image compensation factor.

Light image acquisition is used to compensate for non-uniformity of the light source 30, as well as non-uniformity of the lens and the CCD camera. A light image is read and the pixel values for the light image are recorded. The computer system stores this compensation factor for each pixel and applies it by dividing the corresponding pixel compensation factor by subsequent images pixel values. This error also varies with CCD camera temperature and shutter speed. In the preferred embodiment, the several light images are read and the average over the several images is used to generate the white compensation factor.

Frame transfer error is a known error in CCD cameras, occurring when a new image is read. Smearing occurs from the signal from pixels in a given column. To compensate for this, a short exposure of an image is taken and each pixel value subtracted from the corresponding pixel value of the second normal exposure of the same image which is much longer. The subtraction removes any frame transfer error and is thus completely compensated for.

Scattering errors occur due to the imperfections in the surface finish of the lens, reflections from the surfaces of the lens and from dust particles. To compensate for scattering error, a small opaque object is read and average pixel values for the opaque object and for the entire image are generated. A scatter compensation factor is calculated as the average for the opaque image divided by the average for the entire image. In subsequent images, the scatter compensation factor is multiplied by the average pixel value for the image and the resulting value is subtracted from each pixel in the image.

Image acquisition errors occur as random differences between successive reads of the same image. Depending upon the quality of the results required, several images can be taken and an average image used.

The system is also calibrated with respect to dose. This accomplished by imaging pieces of film exposed to known doses of radiation. The system produces a calibration curve by associating a given level of light intensity with a known dose of radiation. In this way subsequent images can calibrated and rendered in absolute dose.

In addition, the image must be calibrated with respect to distance in order to determine the number of pixels in the X and Y dimensions of the image. In the preferred embodiment, this is accomplished by placing a grid of known dimensions on the light source and calculating the number of pixels per unit distance.

The various compensation factors are stored in the computer for the particular setup. As long as the light source 30 is not moved or adjusted and the shutter speed is not changed, the system remains in calibration. Various pieces of radiochromic film can be placed on the light source and imaged. The raw image is then processed to compensate for the various errors discussed above to produce a precision image that accurately represents the radiation dose applied, such as FIG. 6. Several of these images from three orthogonal planes can be processed using conventional image rendering techniques in order to produce a three dimensional representation of the radiation dose. This information can be used by the medical practitioner to verify radiation treatments specified. Alternatively, this information can be used in any field where it is desirable to verify radiation dose delivery.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. An microdensitometer system for reading an image recorded on radiation sensitive film, said microdensitometer system comprising:

camera means, directed along an imaging axis, for producing image signals representative of said image, said camera means including a planar array of CCD sensing elements extending transverse to said imaging axis, illumination means for producing light uniformly across an imaging plane extending transverse to said imaging axis, said illumination means including an array of light producing elements, a stable voltage reference and a light control means coupled to said array of light producing elements and said stable voltage reference, said light control means including means for sensing the light output of at least one of said light producing elements and means for controlling a level of current to each of said light producing elements in response to said sensed light output, alignment means for adjustably aligning said camera means with respect to said illumination means along said imaging axis.

2. A microdensitometer system according to claim 1 wherein the wavelength of the light producing elements is substantially the same as the peak absorption wavelength of said radiation sensitive film.

3. A microdensitometer system according to claim 2 wherein the wavelength of the light producing elements is 660 nanometers.

4. A microdensitometer system according to claim 1 wherein said illumination means includes a plurality of groups of light producing elements arranged in an array, and said light control means controls the current level applied to each group of light producing elements.

5. A microdensitometer system according to claim 4 wherein each of said groups are annular groups with respect to a central location of said array and the current level applied to at least one group is different from the current level applied to any other group.

6. A microdensitometer system according to claim 5 wherein at least one of said groups is further arranged into two or more subgroups and the same current level is applied to each of said subgroups in said group.

7. A microdensitometer system according to claim 5 comprising three annular groups of light producing elements, an inner group adjacent to said central location of said array, a middle group substantially surrounding said inner group and an outer group substantially surrounding said middle group, and said light control means controls the current level applied to each group, and the current level applied to at least one group is different from the current level applied to any other group, said outer group is further arranged into at least four subgroups and the same current level is applied to each of said subgroups in said outer group, said middle group is further arranged into at least four subgroups and the same current level is applied to each of said subgroups in said middle group, and said inner group is further arranged into at least two subgroups and the same current level is applied to each of said subgroups in said inner group.

8. A microdensitometer system according to claim 1 wherein said light producing elements are arranged in a circular array.

9. A microdensitometer system according to claim 1 wherein said light control means comprises photosensing means for monitoring the intensity of at least one light producing element and for generating an intensity signal representative of the intensity of at least one light producing element, and current control means for regulating the current to at least one of the light producing elements in response to said intensity signal to maintain constant intensity.

10. A microdensitometer system according to claim 9 wherein said illumination means further comprises illumination intensity control means for uniformly adjusting the intensity of each of light producing elements, said intensity control means including means for uniformly adjusting the current supplied to each of said light producing elements.

11. A microdensitometer system according to claim 1 wherein said illumination means includes means for maintaining said stable voltage reference irrespective of ambient temperature.

12. A microdensitometer system according to claim 1 wherein said alignment means includes an optical rail means, extending parallel to said imaging axis, for aligning said camera means along said imaging axis and baseplate means for supporting said optical rail means, said camera means includes means for adjustably positioning said camera means along said optical rail means and said illumination means is moveable in a direction transverse to said imaging axis and includes means for removably securing said illumination means to said baseplate means.

13. A microdensitometer system according to claim 12 wherein said means for removably securing said illumination means to said baseplate means includes a removable magnetic clamp.

* * * * *